United States Patent [19]

Stein et al.

[11] Patent Number: 4,826,915

[45] Date of Patent: May 2, 1989

[54] N-SILYLALKYLAMIDES AND THEIR USE AS ADHESION PROMOTERS IN ROOM TEMPERATURE VULCANIZABLE POLYDIORGANOSILOXANE COMPOSITIONS

[75] Inventors: Judith Stein, Schenectady; Jeffrey H. Wengrovius, Scotia; Lori P. Engle, Clifton Park; David C. Gross, Schenectady; John E. Hallgren, Scotia, all of N.Y.

[73] Assignee: General Electric Company, Schenectady, N.Y.

[21] Appl. No.: 182,695

[22] Filed: Apr. 18, 1988

Related U.S. Application Data

[62] Division of Ser. No. 72,948, Jul. 13, 1987, Pat. No. 4,788,310.

[51] Int. Cl.$^4$ .......................... C08K 5/07; C08G 77/09
[52] U.S. Cl. .................................... 524/731; 524/770; 528/16; 528/17; 528/18; 528/21; 528/34; 528/901

[58] Field of Search .................... 528/18, 901, 21, 34, 528/17, 16; 524/357, 770, 731

[56] References Cited

U.S. PATENT DOCUMENTS

| 3,919,276 | 11/1975 | Le Grow et al. | 556/413 |
| 4,036,813 | 7/1977 | Hardman et al. | 528/34 |
| 4,395,507 | 7/1983 | Dziark et al. | 524/101 |
| 4,460,739 | 7/1984 | Ashby | 524/702 |
| 4,503,209 | 3/1985 | Lucas | 528/18 |
| 4,517,337 | 5/1985 | Lockhart et al. | 524/859 |
| 4,528,353 | 7/1985 | Lucas et al. | 528/21 |
| 4,554,310 | 11/1985 | Wengrovius et al. | 528/18 |

*Primary Examiner*—John C. Bleutge
*Assistant Examiner*—R. Dean, Jr.
*Attorney, Agent, or Firm*—William H. Pittman; James C. Davis, Jr.; James Magee, Jr.

[57] ABSTRACT

N-Silylalkylamides are useful as adhesion promoters in room temperature vulcanizable compositions comprising polyalkyoxysilyl-terminated polydiorganosiloxanes. The formamides, which are preferred, are novel compounds.

12 Claims, No Drawings

N-SILYLALKYLAMIDES AND THEIR USE AS ADHESION PROMOTERS IN ROOM TEMPERATURE VULCANIZABLE POLYDIORGANOSILOXANE COMPOSITIONS

This application is a division of application Ser. No. 072,948, filed July 13, 1987, now U.S. Pat. No. 4,788,310, issued Nov. 29, 1988.

This invention relates to new compositions of matter, and more particularly to room temperature vulcanizable compositions and silicon-nitrogen compounds useful as adhesion promoters therein.

Considerable attention has been directed in recent years to the development of improved one-package room temperature vulcanizable (hereinafter sometimes designated "RTV") compositions. Under ideal conditions, these compositions would be stable for an indefinite period when stored in the absence of moisture, and would promptly cure to a tack-free elastomer upon contact with moisture, including the relatively small proportions of water vapor present in the atmosphere.

In a typical RTV composition, the predominant constituent is a polydiorganosiloxane (hereinafter sometimes designated "silicone" for brevity) containing polyalkoxysilyl end groups, typically dialkkoxyalkylsilyl groups. Said end groups are capable of being crosslinked by atmospheric moisture in the presence of a suitable metal-containing catalyst, usually in aluminum, titanium or tin compound. Disclosures of RTV compositions of this type are present in many patents and publications.

A particularly useful one-package RTV composition is disclosed in U.S. Pat. No. 4,517,337. It employs a catalyst such as dibutyltin bis(acetylacetonate), which is stable in the presence of hydroxy species such as methanol and silanol-terminated silicones and may therefore be employed without scavengers for such hydroxy species.

Many RTV compositions have inadequate adhesion to various substrates, particularly metals such as aluminum and steel. Therefore, it is a common practice to employ adhesion promoters, typically various silicon-nitrogen compounds, in such compositions.

The present invention provides novel RTV compositions containing adhesion promoters, particularly scavenger-free RTV compositions containing tin complex catalyst such as dialkyltin bis(acetylacetonates). It also provides a class of novel silicon-nitrogen compounds useful as adhesion promoters, and a method for their preparation.

In one of its aspects, the present invention includes a method for improving adhesion to a substrate of a room temperature vulcanizable composition comprising a polyalkoxy-terminated polydiorganosiloxane (silicone) and a catalytic amount of a curing catalyst, said method comprising incorporating therein an effective amount, typically about 0.1–5.0 parts per 100 parts of said polyalkoxysilyl-terminated polydiorganosiloxane, of an N-silylalkylamide compound having the formula

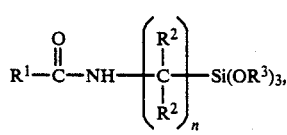

(I)

wherein $R^1$ is hydrogen or an alkyl radical containing from 1 to about 8 carbon atoms, each $R^2$ is independently hydrogen or a primary or secondary alkyl containing from 1 to about 4 carbon atoms, $R^3$ is an alkyl containing from 1 to about 8 carbon atoms and n is from about 2 to about 8.

Another aspect of the invention is RTV compositions comprising (A) at least one polyalkoxy-terminated silicone, (B) a catalytic amount of a curing catalyst, and (C) an amount effective to enhance adhesion to a substrate of said N-silylalkylamide.

In the N-silylalkylamides of the formula I, $R^1$ may be hydrogen or an alkyl group, most often a primary or secondary alkyl group. The formamides, in which $R^1$ is hydrogen, are preferred and are novel compounds. Accordingly, another aspect of the invention is N-silylalkylformamides of formula I wherein $R^1$ is hydrogen.

The $R^2$ radicals may be hydrogen, or alkyl radicals as indicated and are usually hydrogen. $R^3$ is an alkyl radical, usually methyl. The value n is from 2 to about 8 and is preferably 2 or 3, especially 3.

Certain N-silylalkylamides used according to the invention, such as N-(3-trimethoxysilylpropyl)acetamide, are known compounds. Reference is made, for example, to U.S. Pat. No. 3,919,276 for their preparation.

The N-silylalkylformamides may be prepared by the reaction of an alkyl alkanoate having the formula

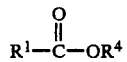

with an aminoalkylsilane of the formula

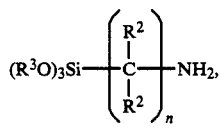

wherein $R^{1-3}$ and n are as previously defined and $R^4$ is $C_{1-4}$ alkyl and especially methyl. This reaction is most conveniently conducted by heating a mixture of the two reagents at room temperature of about 30°–80° C., preferably in an inert atmosphere such as nitrogen, with removal of the by-product $R^4OH$ by distillation. A solvent may be employed but is seldom necessary. Most often, the alkyl alkanoate is used in excess, typically in a molar ratio of about 5–10:1. When the reaction is complete, conventional methods of product isolation may be used where necessary. However, the preparation of formamides by the use of such low boiling esters as methyl formate produces only volatile by-products and purification operations may then be unnecessary.

The polyalkoxysilyl-terminated silicones useful as component A in the RTV compositions of this invention may be represented by the formula

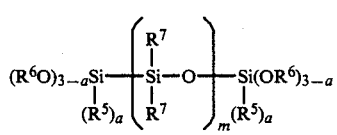

(II)

wherein R[5] is an unsubstituted or substituted hydrocarbon radical containing from 1 to about 13 carbon atoms, R[6] is an alkyl, alkoxyalkyl, acylalkyl, acyloxyalkyl or cyanoalkyl radical containing from 1 to about 8 carbon atoms or an aralkyl radical containing from 1 to about 14 carbon atoms, each R[7] is independently an unsubstituted or substituted hydrocarbon radical containing about 1-13 carbon atoms, a is 0 or 1 and m is in the range of about 5-5000. Illustrative R[5] and R[7] radicals are methyl, ethyl, phenyl, trifluoropropyl and vinyl. Alkyl radicals having up to about 4 carbon atoms and especially methyl radicals are preferred. R[6] may be alkyl or the designated substituted alkyl radicals containing aryl, ethyl, ester ketone or cyano substituents; it is also most often $C_{1-4}$ alkyl and especially methyl. The value of a is 0 or 1 and most often 1.

Component A may be prepared in situ in the RTV composition by the reaction of a silanol-terminated silicone and, as an endcapping reagent, a polyalkoxysilane such as methyltrimethoxysilane, in accordance with U.S. Pat. No. 4,395,526. It may also be previously formed by the same reaction, most often in the presence of a catalyst as disclosed, for example, in U.S. Pat. No. 4,515,932 and copending, commonly owned application Ser. No. 225,992, filed 7/29/88. The time of its formation is not critical for the purposes of this invention, although it is frequently preferred to employ a previously formed polyalkoxysilyl-terminated silicone.

Component B, the curing catalyst, may be any of the metal-containing catalysts known in the art. As previously noted, these are usually aluminum, titanium or tin compounds. In a particularly preferred embodiment of the invention, the catalyst is an organotin complex of the formula

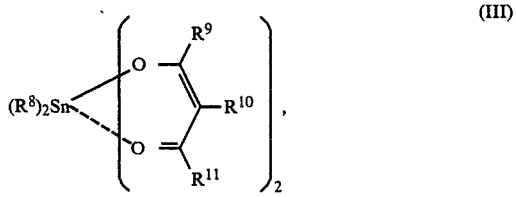

(III)

wherein R[8] is an unsubstituted or substituted hydrocarbon radical containing from 1 to about 18 carbon atoms; each of R[9], R[10] and R[11] is independently hydrogen, R[12], Si(R[12])$_3$, acyl or nitrile; and R[12] is an unsubstituted or substituted hydrocarbon radical containing from 1 to about 18 carbon atoms. Compositions containing such complexes, especially di-n-butyltin bis(acetylacetonate), are disclosed and claimed in the aforementioned U.S. Pat. No. 4,517,337, the disclosure of which is incorporated by reference herein.

Component C, the N-silylalkylamide, is employed in the RTV composition as an adhesion promoter. Its action as such is frequently optimized if it is employed in combination with (D) a cyanoalkyltrialkoxysilane, most often 2-cyanoethyltrimethoxysilane (hereinafter "CETMS") or 3-cyanopropyltrimethoxysilane, which acts as a synergist therefor.

Components B and C are present in the RTV compositions of this invention in effective proportions to serve as catalyst and adhesion promoters, respectively. In general, about 0.1-10.0 parts of component B and about 0.1-5.0 parts of component C are employed per 100 parts of component A. When employed, component D is usually present in the amount of about 0.1-5.0 parts per 100 parts of component A.

The RTV compositions of the invention may also contain other constituents in common use in such compositions, including curing catalyst accelerators, scavengers for hydroxy species, plasticizers, pigments and fillers. In particular, at least one of the following may be present all proportions being per 100 parts of component A:

(E) about 0.05-5.0 parts of a diketone of the formula

(IV)

wherein $R^{9-11}$ are as previously defined;

(F) about 0.01-10.0 parts of at least one polyalkoxysilane of the formula

(V)

wherein $R^{5-6}$ and a are as previously defined;

(G) about 1-50 parts of a plasticizer;

(H) about 5-700 parts of at least one filler; and (J) about 0.1-5.0 parts of an amine or guanidine as a curing accelerator.

Components E and F are often particularly preferred other constituents. Their presence contributes to the shelf stability of the RTV composition in the absence of moisture and its rapidity of cure in the presence of moisture.

The presence of component G is also frequently preferred. Suitable plasticizers useful as component G include trialkylsilyl-terminated polydiorganosiloxanes of the formula

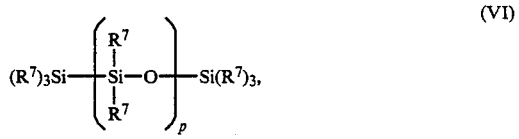

(VI)

wherein R[7] is as previously defined and p is in the range of about 25-5000.

The presence or absence of component H, the filler, will depend to some extent on the intended use of the RTV composition. When the composition is to be used as a construction sealant or caulking compound, relatively large proportions of filler may be employed. For other uses, minor proportions of filler or no filler may be advisable. Suitable fillers include reinforcing materials such as silica aerogel, fumed silica, precipitated silica, glass fibers, titanium dioxide, zirconium silicate, iron oxide, calcium carbonate, diatomaceous earth and carbon black, and extending materials such as ground quartz and polyvinyl chloride, as well as mixtures thereof. It is frequently advantageous to pretreat a silica filler with an activating agent such as octamethylcyclotetrasiloxane.

Various amines and guanidines, optionally alkoxysilyl-substituted, are known to be useful as curing accelerators (component J). Suitable accelerators are disclosed, for example, in the aforementioned U.S. Pat. No. 4,517,337.

The preparation and properties of the compositions of the present invention is illustrated by the following examples. Parts are by weight. All RTV compositions were prepared by conventional high-shear mixing techniques in a nitrogen atmosphere, under the equivalent of "dry box" conditions. Viscosities are Brookfield viscosities at 25° C.

Example 1

A mixture of 7 parts (39 mmol.) of 3-aminopropyltrimethoxysilane and 20 parts (330 mmol.) of methyl formate was heated under reflux in a nitrogen atmosphere. The reaction was monitored by gas chromatography and was found to be complete after 3 hours. Volatiles were then removed in vacuum, yielding the desired N-(3-trimethoxysilylpropyl)formamide.

Example 2

An RTV composition was prepared by initially blending 100 parts of a polymethoxysilyl-terminated polydimethylsiloxane having a viscosities of 300 poises, 1 part of CETMS, 16 parts of octamethylcyclotetrasiloxane-treated fumed silica and 23 parts of a trimethylsilyl-terminated polydimethylsiloxane oil, and subsequently adding 0.42 part of dibutyltin bis(actylacetonate), 0.28 parts of acetylacetone, 0.35 part of methyltrimethoxysilane and 0.7 part of the product of Example 1. Adhesion-in-peel on unprimed aluminum was determined according to ASTM test method C794 after 7 days of cure at 50% relative humidity. Comparison was made with a control in which 0.7 part of glycidoxypropyltrimethoxysilane was substituted for the product of Example 1.

The product of Example 1 gave an adhesion value of 179.3 millipascals, while the control gave a value less than 35 millipascals.

What is claimed is:

1. A room temperature vulcanizable composition comprising (A) at least one polyalkoxy-terminated polydiorganosiloxane, (B) a catalytic amount of a curing catalyst, and (C) an amount effective to enhance adhesion to a substrate of an N-silylalkylamide compound having the formula

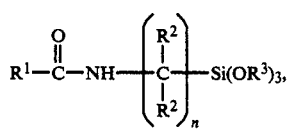

(I)

wherein $R^1$ is hydrogen or an alkyl radical containing from 1 to about 8 carbon atoms, each $R^2$ is independently hydrogen or a primary or secondary alkyl radical containing from 1 to about 4 carbon atoms, $R^3$ is an alkyl radical containing from 1 to about 8 carbon atoms and n is from 2 to about 8.

2. A composition according to claim 1 wherein component B is an aluminum, titanium or tin compound and is employed in the amount of about 0.1-10.0 parts by weight per 100 parts of component A.

3. A composition according to claim 2 wherein component B is an organotin complex of the formula

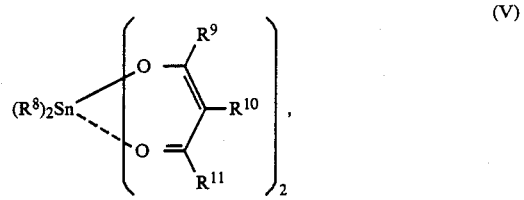

(V)

wherein $R^8$ is an unsubstituted or substituted hydrocarbon radical containing from 1 to about 18 carbon atoms; each of $R^9$, $R^{10}$ and $R^{11}$ is independently hydrogen, $R^{12}$, $Si(R^{12})_3$, acyl or nitrile; and $R^{12}$ is an unsubstituted or substituted hydrocarbon radical.

4. A composition according to claim 3 wherein about 0.1-10.0 parts of component B and about 0.1-5.0 parts of component C are employed per 100 parts of component A.

5. A composition according to claim 4 wherein each of $R^9$ and $R^{11}$ is methyl and $R^{10}$ is hydrogen.

6. A composition according to claim 4 which also comprises at least one of the following, all proportions being per 100 parts of component A:
(E) about 0.05-5.0 parts of a diketone of the formula

(VI)

wherein each of $R^9$, $R^{10}$ and $R^{11}$ is independently hydrogen, $R^{12}$, $Si(R^{12})_3$, acyl or nitrile; and $R^{12}$ is an unsubstituted or substituted hydrocarbon radical;
(F) about 0.01-10.0 parts of at least one polyalkyloxysilane of the formula

(VII)

wherein $R^5$ is an unsubstituted or substituted hydrogen radical containing from 1 to about 13 carbon atoms, $R^6$ is an alkyl, alkoxyalkyl, acylalkyl, acyloxyalkyl or cyanoalkyl radical containing from 1 to about 8 carbon atoms or an aralkyl radical containing from 1 to about 14 carbon atoms, and a is 0 or 1;
(G) about 1-50 parts of a plasticizer;
(H) about 5-700 parts of at least one filler; and
(J) about 0.1-5.0 parts of an amine or guanidine as a curing accelerator.

7. A composition according to claim 6 wherein $R^1$ is hydrogen.

8. A composition according to claim 7 wherein $R^2$ is hydrogen.

9. A composition according to claim 8 wherein $R^3$ is methyl and n is 3.

10. A composition according to claim 9 which also comprises (D) a cyanoalkyltrialkoxysilane in the amount of about 0.1-5.0 parts per 100 parts of component A.

11. A composition according to claim 10 which also comprises components E, F and G, wherein component G is at least one trialkylsilyl-terminated polydiorganosiloxane of the formula

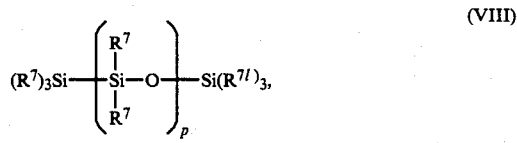

(VIII)

wherein $R^7$ is an unsubstituted or substituted hydrocarbon radical containing about 1-13 carbon atoms and p is in the range of 25-5000.

12. A composition according to claim 9 wherein each of $R^9$ and $R^{11}$ is methyl and $R^{10}$ is hydrogen.

* * * * *

UNITED STATES PATENT AND TRADEMARK OFFICE
CERTIFICATE OF CORRECTION

PATENT NO. : 4,826,915

DATED : May 2, 1989

INVENTOR(S) : Judith Stein et al.

It is certified that error appears in the above-identified patent and that said Letters Patent is hereby corrected as shown below:

Column 2, line 65,

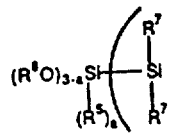

should read

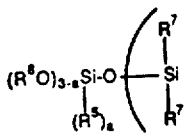

Column 4, line 40,

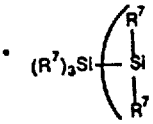

should read

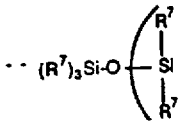

Column 6, line 60,

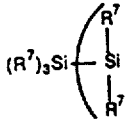

UNITED STATES PATENT AND TRADEMARK OFFICE
CERTIFICATE OF CORRECTION

PATENT NO. : 4,826,915

DATED : May 2, 1989

INVENTOR(S) : Judith Stein, et al.

It is certified that error appears in the above-identified patent and that said Letters Patent is hereby corrected as shown below:

should read 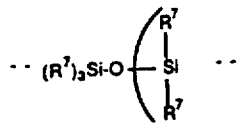

Signed and Sealed this

Thirtieth Day of November, 1993

Attest:

BRUCE LEHMAN

*Attesting Officer*    *Commissioner of Patents and Trademarks*